(12) United States Patent
Li et al.

(10) Patent No.: US 9,572,706 B2
(45) Date of Patent: Feb. 21, 2017

(54) HEAD SUPPORT FOR OPERATING TABLES

(71) Applicant: MAQUET GMBH, Rastatt (DE)

(72) Inventors: Hongquiang Li, Suzhou Jiangsu (CN); Kaiyou Ge, Changzhou Jiangsu (CN)

(73) Assignee: MAQUET GMBH, Rastatt (DE)

( * ) Notice: Subject to any disclaimer, the term of this patent is extended or adjusted under 35 U.S.C. 154(b) by 250 days.

(21) Appl. No.: 14/058,999

(22) Filed: Oct. 21, 2013

(65) Prior Publication Data

US 2014/0116450 A1 May 1, 2014

(30) Foreign Application Priority Data

Oct. 29, 2012 (EP) .................................... 12190367

(51) Int. Cl.
*A61F 5/37* (2006.01)
*A61G 13/12* (2006.01)

(52) U.S. Cl.
CPC ............ *A61F 5/3707* (2013.01); *A61G 13/121* (2013.01); *A61G 13/1205* (2013.01)

(58) Field of Classification Search
CPC ..... A47C 20/02; A61B 6/0421; A61B 6/0428; A61B 19/203; A61B 19/28; A61F 5/3707; A61G 7/07; A61G 7/072; A61G 13/121; A61G 15/125; A61G 13/1205
USPC ............................................ 5/622, 637, 640
See application file for complete search history.

(56) References Cited

U.S. PATENT DOCUMENTS

| | | | |
|---|---|---|---|
| 1,278,251 A * | 9/1918 | Syjud | G01B 3/56 33/455 |
| 2,535,559 A | 3/1949 | Wolf | |
| 4,034,748 A * | 7/1977 | Winner | A61F 5/05883 128/870 |
| 4,545,572 A | 10/1985 | Day | |
| 5,154,186 A | 10/1992 | Laurin et al. | |
| 5,515,867 A | 5/1996 | Lamb | |
| 6,594,839 B1 * | 7/2003 | Papay | A61B 19/203 297/405 |
| 6,648,416 B2 * | 11/2003 | O'Connor | A47C 7/383 297/397 |

(Continued)

FOREIGN PATENT DOCUMENTS

| | | |
|---|---|---|
| CN | 2582584 Y | 10/2003 |
| CN | 101123933 A | 2/2008 |

(Continued)

OTHER PUBLICATIONS

English translation of Chinese Office Action for Application No. 201310498831.1 dated Jun. 3, 2015.
European Search Report for EP 12190367.8 dated Mar. 4, 2013.

*Primary Examiner* — Nicholas Polito

(57) ABSTRACT

The invention relates to a head support (10, 100) for operating tables, comprising a rotatably mounted first holding element (12) for surrounding a first side of a patient's head receivable in a receiving area (32) and an also rotatably mounted second holding element (14) for surrounding a second side of the head. The two holding elements (12, 14) are coupled to each other in a coupling area by means of a coupling element (16) such that when one of the holding elements (12, 14) is rotated, the coupling element (16) also rotates the other holding element (12, 14). Between the coupling area and the receiving area (32) a stationarily arranged supporting element (33) for supporting the head receivable in the receiving area (32) is provided.

20 Claims, 8 Drawing Sheets

(56) References Cited

U.S. PATENT DOCUMENTS

| | | | |
|---|---|---|---|
| 7,263,733 B2 | 9/2007 | Fujita et al. | |
| 2002/0073487 A1* | 6/2002 | Phillips | A61F 5/055 5/628 |
| 2002/0169460 A1 | 11/2002 | Foster et al. | |
| 2011/0035882 A1 | 2/2011 | Lijun | |

FOREIGN PATENT DOCUMENTS

| | | |
|---|---|---|
| DE | 43 42 971 C1 | 3/1995 |
| EP | 1 219 276 B1 | 8/2006 |
| JP | S4915434 Y1 * | 4/1974 |
| JP | S58-1447 | 1/1983 |
| WO | 00/66059 A2 | 9/2000 |
| WO | 01/49223 A1 | 7/2001 |

* cited by examiner

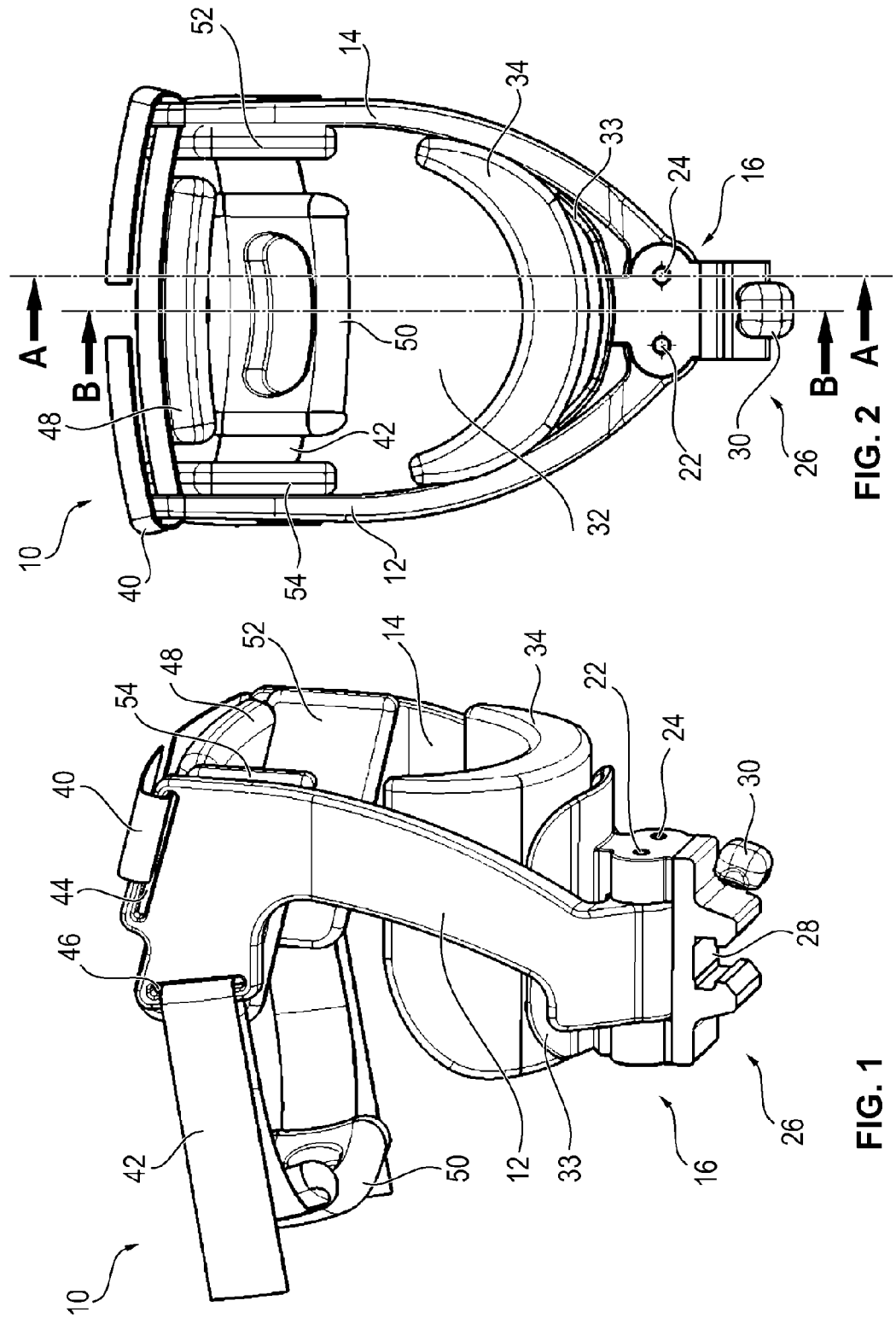

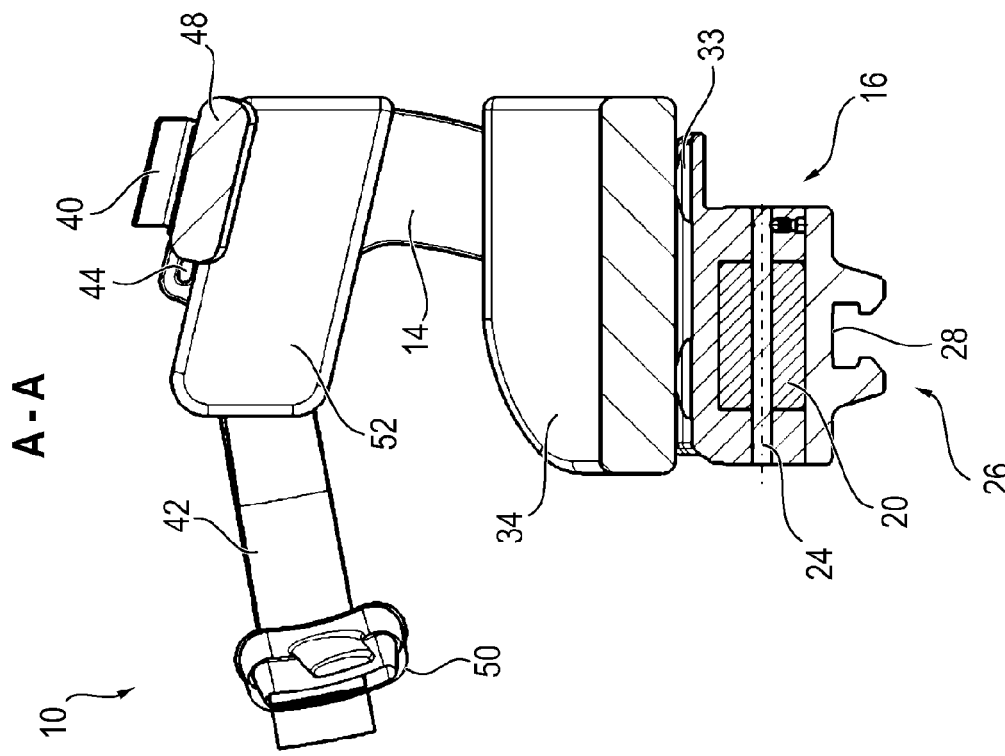
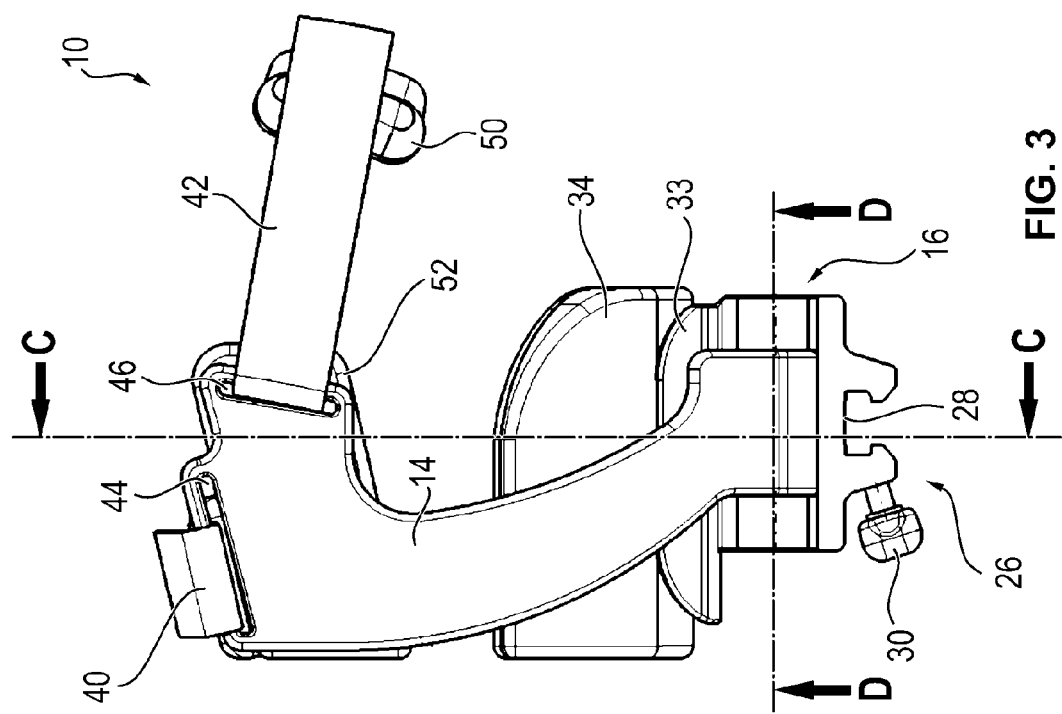

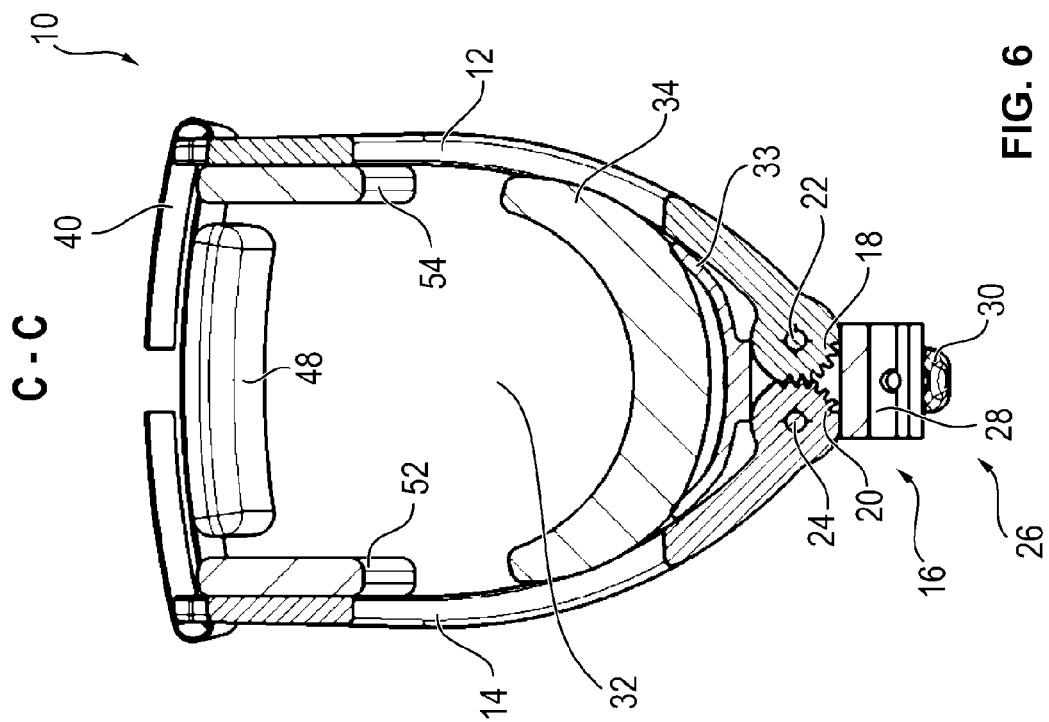
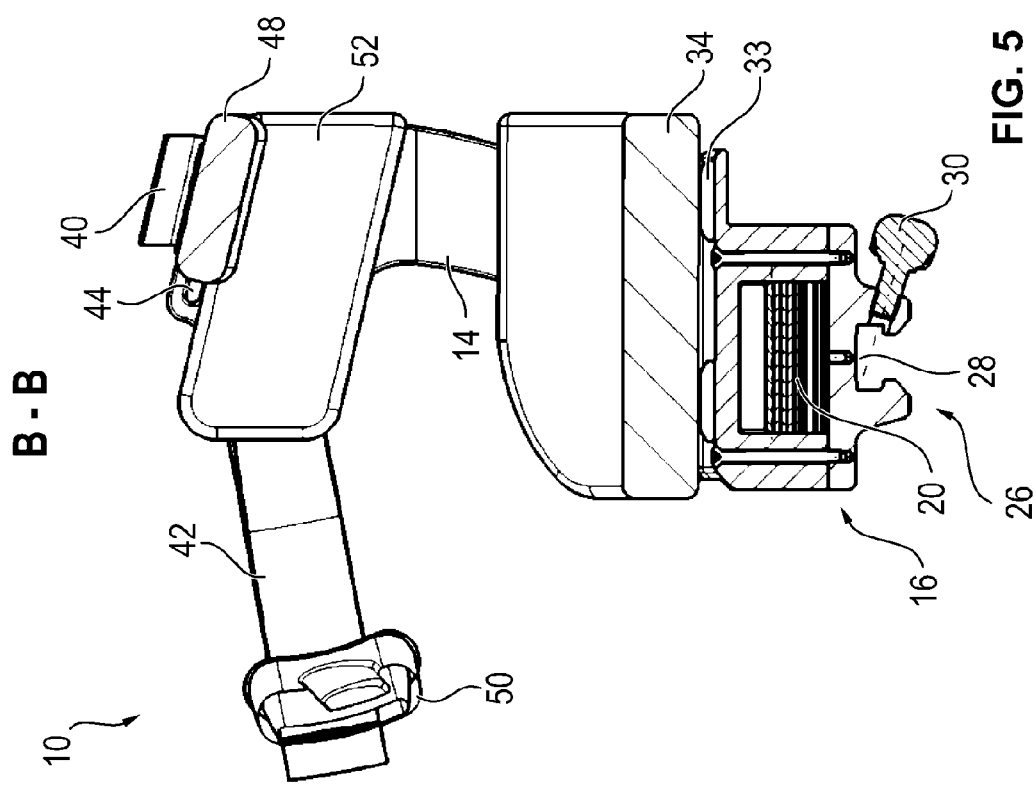

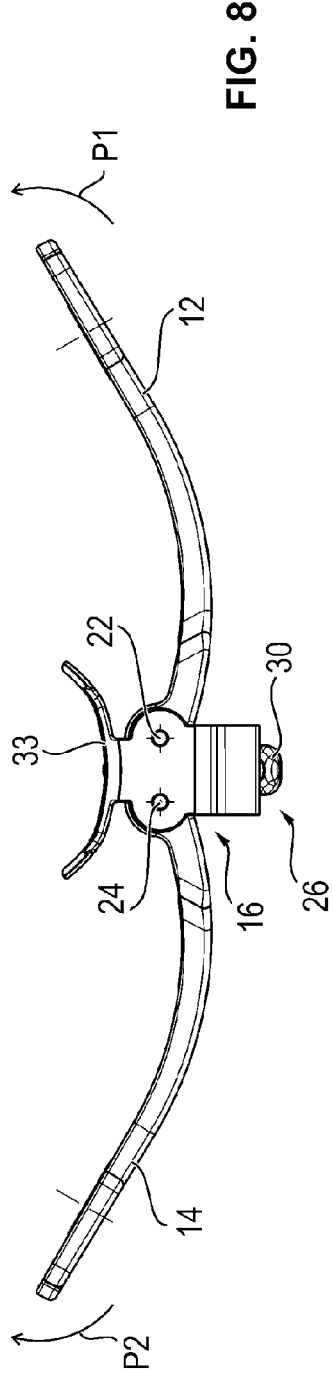
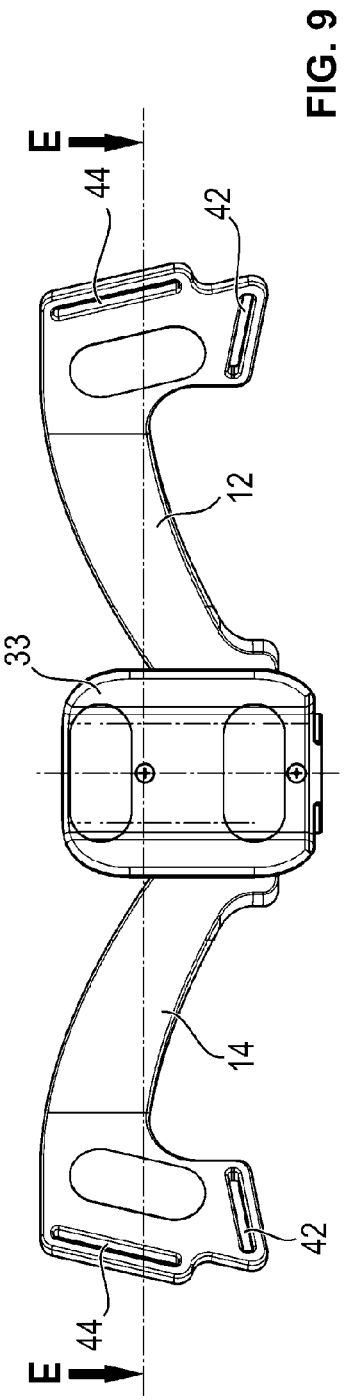
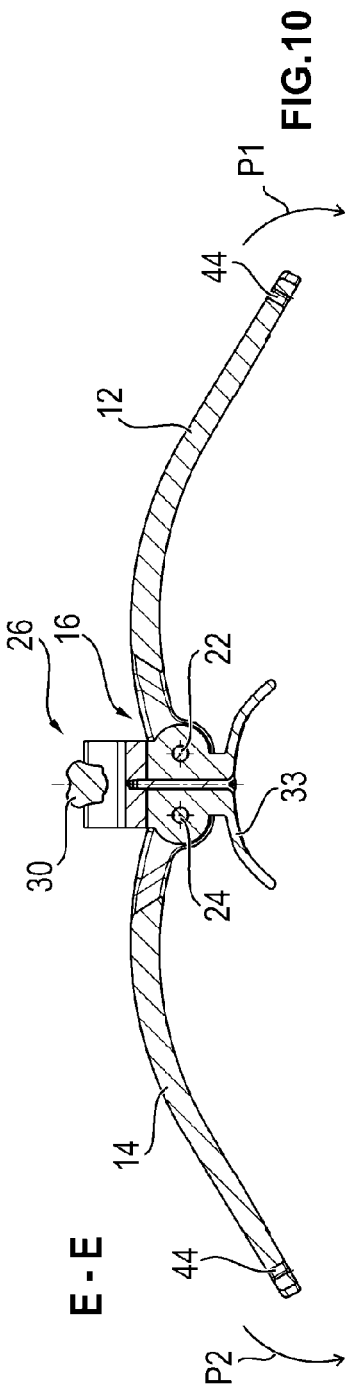

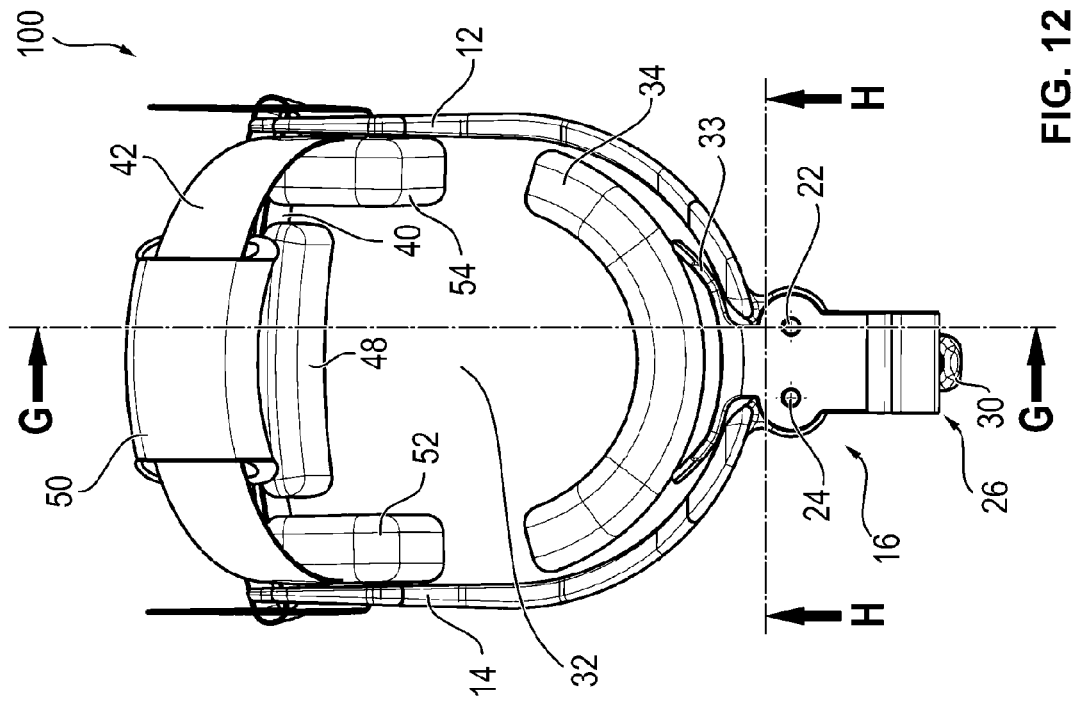
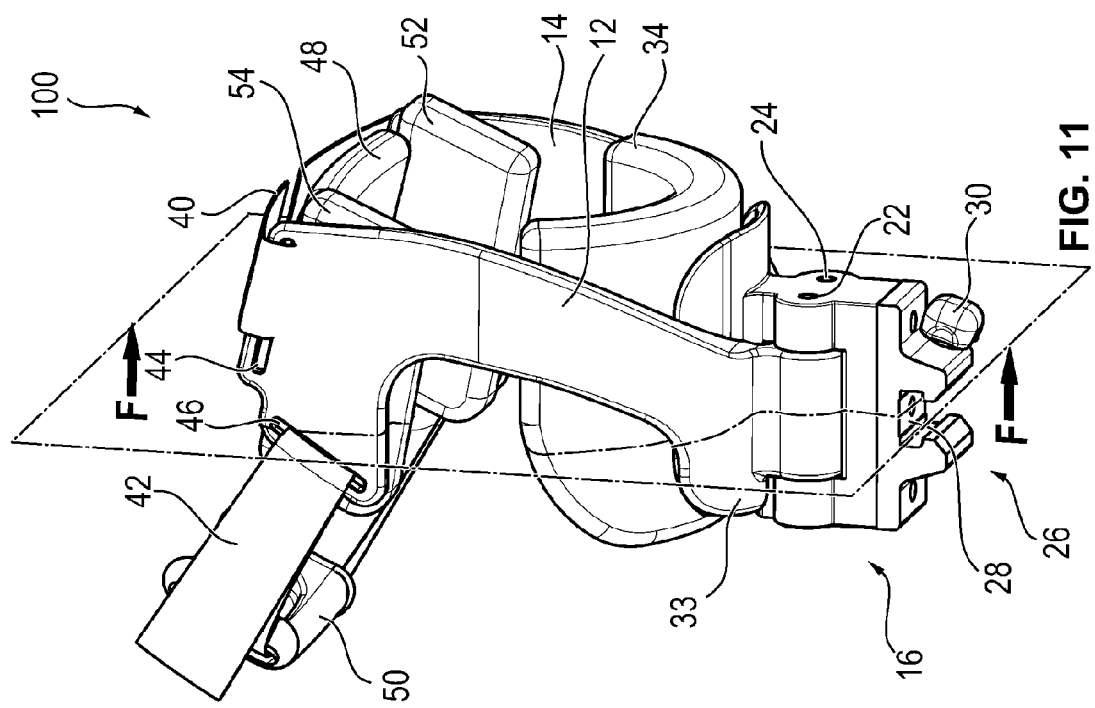

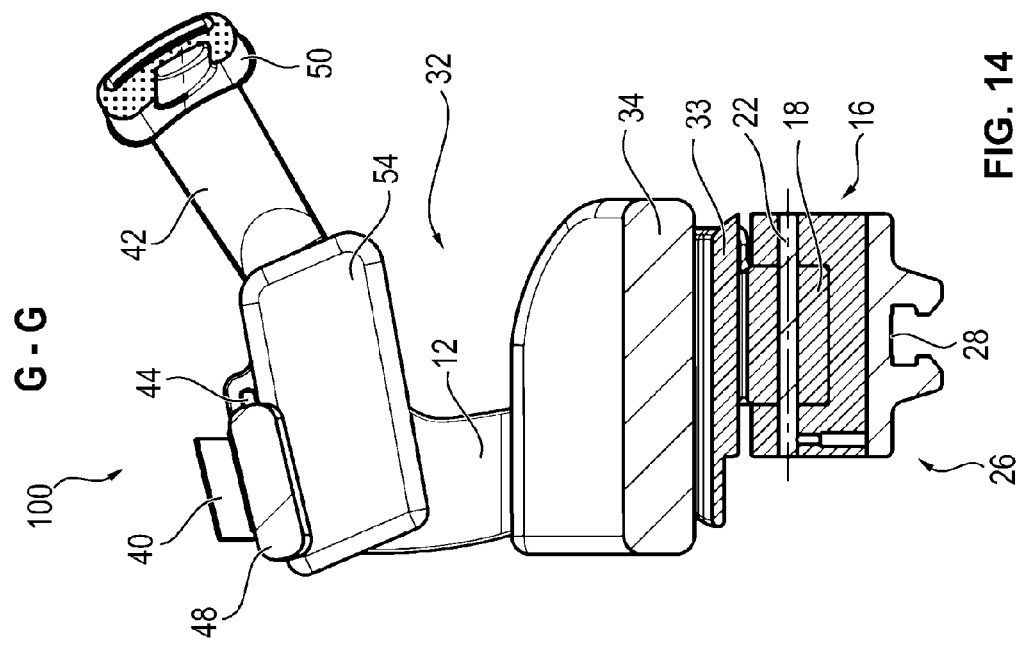
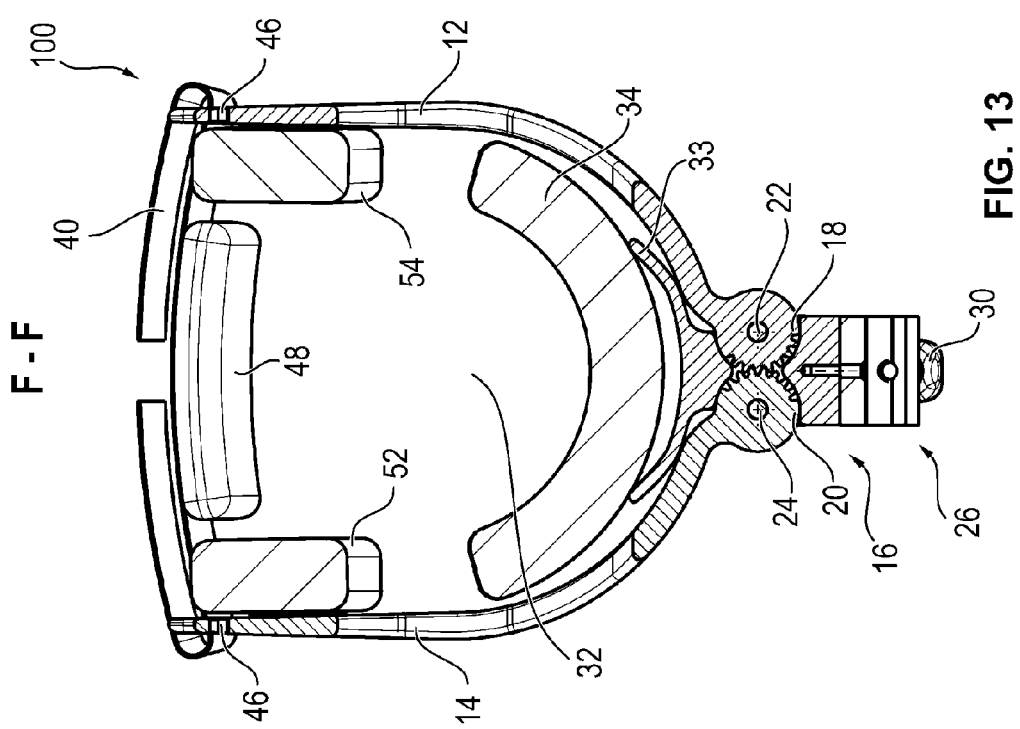

HEAD SUPPORT FOR OPERATING TABLES

CROSS REFERENCE TO RELATED APPLICATIONS

Applicant hereby claims foreign priority benefits under U.S.C. §119 from European Utility Model Application No. 12 190 367.8 filed on Oct. 29, 2012, the contents of which are incorporated by reference herein.

TECHNICAL FIELD

The invention relates to a head support for operating tables comprising a first holding element rotatably mounted about a first axis of rotation for surrounding a first side of a patient's head receivable in a receiving area of the head support and a second holding element rotatably mounted about a second axis of rotation for surrounding a second side of the patient's head. The first holding element and the second holding element are coupled to each other in a coupling area by means of at least one coupling element such that when one of the holding elements is rotated, the coupling element also rotates the other holding element.

BACKGROUND

During surgeries in the shoulder area the patient is usually supported lying on the back on the operating table. For supporting the head a head support is attached to the operating table by means of which a secure fixing of the head during the surgery shall take place to guarantee thus a secure performance of the surgery being as low risk as possible for the patient.

From Document US 2002 0169460 A1 a head support is known comprising two holding elements, each laterally surrounding the patient's head which are coupled to each other in a coupling area. To this end, an arcuate oblong hole is provided in one of the two holding elements, in which a pin connected to the other holding element is guided. Thus it is achieved that when opening or closing one of the holding elements, the other holding element is also rotated along and is thus also opened or closed. One problematic aspect of this coupling is that the coupling via the oblong hole and the pin is relatively unstable and can easily get caught and a synchronous opening and closing is not ensured. Another problematic aspect is that the patient's back of the head, which is arranged in the area of the coupling, can easily get caught which may cause injuries.

Further head supports are known from Documents U.S. Pat. No. 5,154,186 A, U.S. Pat. No. 2,535,559 A, U.S. Pat. No. 4,545,572 A, WO 0066059 A3, U.S. Pat. No. 4,034,748 A, WO 0149223 A1, U.S. Pat. No. 7,263,733 B2, US 20110035882 A1 and EP 1219276 B1.

SUMMARY

It is the object of the invention to provide a head support for operating tables, the holding elements of which are securely adjustable in an easy manner.

This object is solved by a head support with the features of claim 1. Advantageous embodiments of the invention are specified in the dependent claims.

According to the invention a stationarily arranged supporting element for supporting the head receivable in the receiving area is provided between the coupling area and the receiving area. Due to this element it is prevented that when opening and closing the holding elements, i.e. when they are rotated about the respective axis of rotation, the head can be trapped by the coupling element. Further, vice versa it is also ensured that the coupling between the two holding elements takes place reliably so that when one of the holding elements is adjusted, the other one is automatically adjusted as well and thus an easy and safe handling is possible.

Stationarily arranging the supporting element means in this connection in particular that the supporting element is not moved along when the first holding element and/or the second holding element is rotated, but has a constant position relative to the other components of the head support and/or of the operating table.

The supporting element in particular has an arcuate support surface for supporting the patient's back of the head so that it can be held ergonomically and sliding can be prevented. In particular, the supporting element has a likewise arcuate padding so that an even more comfortable support of the back of the head is guaranteed. Arcuate support surface means in particular that the support surface is ergonomically adapted to the contour of a back of the head and thus has a bowl-shaped or segmented cylindrical structure.

It is in particular advantageous when the coupling element includes at least one cog wheel segment. In a particular advantageous embodiment, the coupling element includes a first cog wheel segment and a second cog wheel segment, wherein the first cog wheel segment is firmly connected to the first holding element and the second cog wheel segment is firmly connected to the second holding element. The two cog wheel segments are in engagement with each other by their teeth meshing with each other. Due to the two cog wheel segments it is achieved that when the first holding element is rotated about the first axis of rotation, the second holding element is rotated synchronously about the second axis of rotation so that a synchronous opening and closing of the two holding elements takes place. The coupling via cog wheel segments further has the advantage that a stable, reliable coupling takes place. The holding elements are rigidly connected to the respective cog wheel segment.

In an alternative embodiment, "whole" cog wheels can be provided instead of cog wheel segments. Here, respectively one cog wheel is coupled, preferably rigidly connected, with respectively one of the holding elements.

It is in particular advantageous when the first cog wheel segment and the first holding element and/or the second cog wheel segment and the second holding element are respectively integrally formed. In particular, the first holding element and the first cog wheel segment and/or the second holding element and the second cog wheel segment are made of plastics in an injection moulding process. Thus, easy manufacturing of stable elements without join patches is possible. The assembly is simplified as well.

The head support is in particular formed such that it is formed symmetrically to a centre plane of the head support. Thus, in particular the first holding element and the second holding element are mirror-symmetrical to said centre plane.

The head support in particular has a fastening element for fastening the head support on an operating table. The fastening element preferably includes a receiving area by which the fastening element can be slid on a complementary formed rail of the operating table, wherein said rail is then partially received in the receiving area. Via a set screw the head support can be fixed on said rail so that sliding is prevented.

The coupling element is in particular arranged between the fastening element and the supporting element so that a simple compact structure is achieved and still injuries are prevented.

In a particularly preferred embodiment, a first belt for connecting the two holding elements is provided. Via said first belt the two holding elements can be connected to each other in particular when they surround the patient's head in a closed state so that the two holding elements are securely held together and thus a reliable fixing of the head takes place.

In a particularly advantageous embodiment, in addition to the first belt a second belt for connecting the two holding elements is provided which also serves in particular to connect the two holding elements to each other in the closed state so that the head received between them is reliably fixed.

The first belt is in particular arranged at the holding elements such that it surrounds the forehead of the patient, wherein the second belt is in particular arranged such that it surrounds the chin of the patient.

The coupling element is in particular arranged respectively at a first end portion of the two holding elements. The first belt and/or the second belt are arranged at a second end portion of the first holding element opposite to the first end portion of the first holding element and at a second end portion of the second holding element opposite to the first end portion of the second holding element. Thus, via the two holding elements and the two belts the head is completely surrounded, so that a reliable fixing takes place.

The first holding element and/or the second holding element are in particular formed of an elastic material so that they can adapt to the shape of the head and injuries can be prevented despite a secure fixing. Here, the two holding elements are in particular formed such that respectively at an action of force of 250 N at the end of first/second holding element, where the belts contact the first/second holding element, an elastic deformation between 10 mm and 20 mm, in particular between 12 mm and 18 mm, occurs.

In a closed state, the two holding elements and the supporting element surround the patient's head together at at least three sides so that a secure fixing takes place. By a corresponding rotation of one of the holding elements or of both holding elements they can be pivoted from a closed state into an open state at which the patient's head is not surrounded. In the open state the patient can thus be positioned in the receiving area in an easy manner, wherein in the closed state a secure fixing of the head takes place.

The coupling element and the holding elements are in particular designed such that the holding elements in the open state can serve as support for the arms of a person treating the patient. To this end, they are in particular rigidly formed in a manner to reliably support the arms. In this manner, a person treating the patient can support his/her forearms on the holding elements, i.e. while he/she intubates the patient. Here, the support ensures that the tube can be safely introduced.

The holding elements are also referred to as wings due to their corresponding shape and flexibility.

BRIEF DESCRIPTION OF THE DRAWINGS

Further features and advantages of the invention result from the following description which explains the invention in more detail with reference to embodiments in connection with the enclosed Figures in which:

FIG. 1 shows a schematic, perspective illustration of a head support according to a first embodiment;

FIG. 2 a rear view of the head support according to FIG. 1;

FIG. 3 a side of the head support according to FIGS. 1 and 2;

FIG. 4 a lateral sectional illustration of the head support according to FIGS. 1 to 3 along the section A-A;

FIG. 5 a further lateral sectional illustration of the head support according to FIGS. 1 to 4 along the section B-B;

FIG. 6 a sectional front view of the head support according to FIGS. 1 to 5 along the section C-C;

FIG. 8 a simplified illustration of the head support according to FIGS. 1 to 7 in an open state;

FIG. 9 a further simplified illustration of the head support according to FIGS. 1 to 8 in the open state;

FIG. 10 a sectional illustration of the head support according to FIGS. 1 to 9 in the open state along the section E-E;

FIG. 11 a perspective illustration of a head support according to a second embodiment;

FIG. 12 a front view of the head support according to FIG. 11;

FIG. 13 a sectional front view of the head support according to FIGS. 11 and 12 along the section F-F;

FIG. 14 a sectional side view of the head support according to FIGS. 11 to 13 along the section G-G;

DETAILED DESCRIPTION OF THE PREFERRED EMBODIMENT

Figure 7:
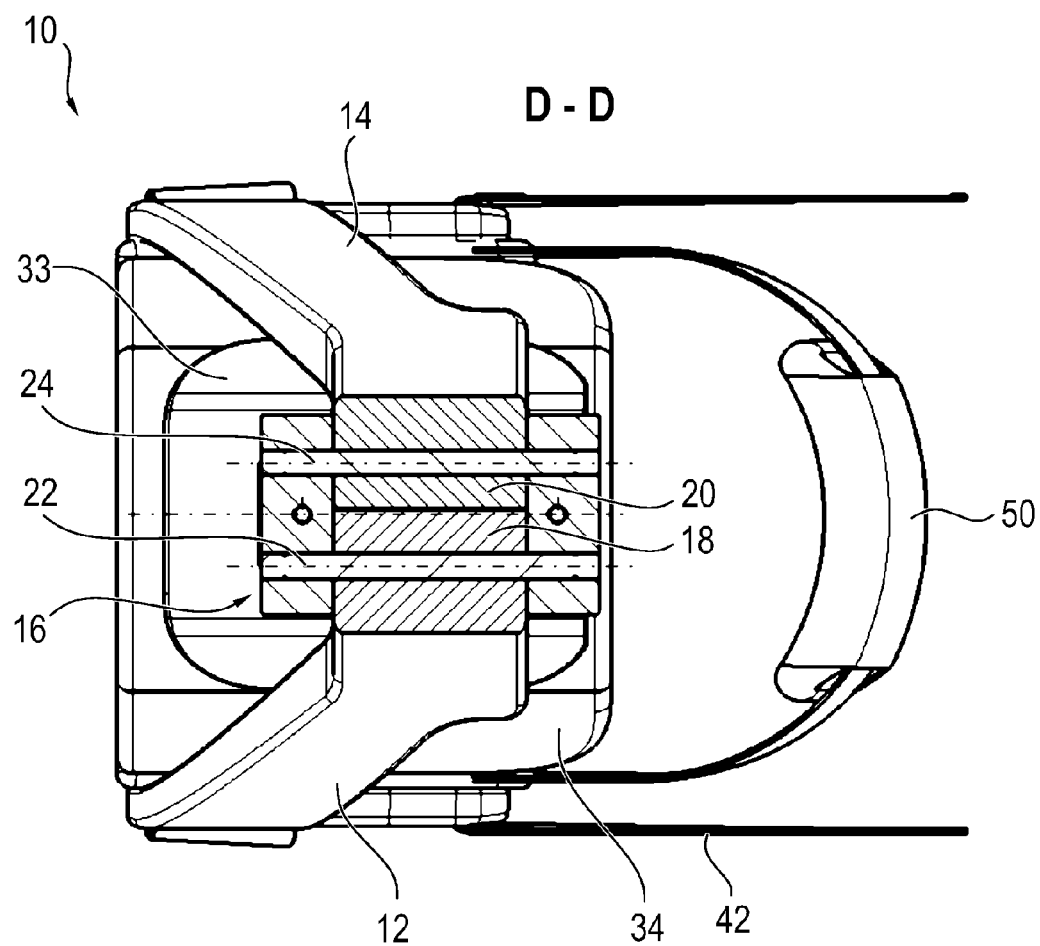
FIG. 7 a sectional bottom view of the head support according to FIGS. 1 to 6 along the section D-D.

In FIG. 1, a schematic illustration of a head support 10 for operating tables according to a first embodiment is illustrated. The head support 10 is in particular attached to a non-illustrated operating table in order to support and securely fix the head of the patient to be operated during shoulder surgeries.

Here, the patient is in particular positioned on the back on the operating table, i.e. face up.

In FIG. 2, a rear view and in FIG. 3 a side view of the head support 10 according to FIG. 1 is shown. FIGS. 4 to 7 respectively show a sectional illustration of the head support 10, wherein in FIGS. 4 and 5 respectively a side view, in FIG. 6 a front view and in FIG. 7 a bottom view is illustrated. FIGS. 8 and 9 respectively show a highly simplified illustration of the head support 10 in the open state. FIG. 10 also shows the head support 10 in the open state as sectional illustration. In the following, the structure and the function of the head support 10 with respect to FIGS. 1 to 10 are explained in more detail.

The head support 10 includes two wing-like formed holding elements 12, 14 which are coupled to each other via a coupling element 16 such that they can be pivoted synchronously from a closed state illustrated in FIGS. 1 to 7 in an open state illustrated in FIGS. 8 to 10.

The coupling element 16 comprises a first cog wheel segment 18 integrally formed with the first holding element 12 and a second cog wheel segment 20 integrally formed with the second holding element 20 which mesh with each other and are thus in engagement with each other. The first holding element 12 is rotatably mounted about a first axis of rotation 22 and the second holding element 14 is rotatably mounted about a second axis of rotation 24. Due to the coupling via the two cog wheel segments 18, 20 it is achieved that, when one of the two holding elements 12, 14 is rotated about its respective axis of rotation 22, 24, the respective other holding element 12, 14 is correspondingly rotated along about its axis of rotation 22, 24 via the coupling. Thus, a synchronous closing and opening of the two holding elements 12, 14 is achieved, when only one of the holding elements 12, 14 is actuated.

The cog wheel segments 18, 20 also have the effect that a stable coupling takes place so that the two holding elements 12, 14 can be used for supporting the arms of a physician in the open state. In particular, the physician can thus support himself on the holding elements, when he intubates the patient already supported on the operating table and with his head in the head support 10 before the surgery.

Further, the head support 10 comprises a fastening element 26 by means of which the head support 10 is fastenable on the operating table. To this end, in particular a rail is provided at the operating table which is formed complementary to a receiving area 28 of the fastening element 26 so that the fastening element 26 can be slid on said rail. Via a rotary knob 30 the head support 10 can be fixed at the desired position on the rail so that undesired sliding is prevented.

Further, the head support 10 includes a supporting element 33 which is arranged between the cog wheel segments 18, 20 and the receiving area 32 in which the patient's head is received. On the supporting element 33 in particular a padding 34 is provided on which the patient's back of the head is supported. To this end, the supporting element 33 and/or the padding 34 are in particular arcuately shaped and thus adapted to the ergonomics of a human being's back of the head.

For supporting the patient the head support 10 is arranged in the open state shown in FIGS. 8 to 10 so that the head can be comfortably received in the receiving area 32 and lies via the back of the head on the padding 34. Subsequently, one of the two holding elements 12, 14 is rotated in the direction of the arrow P1 or the arrow P2 and thus brought from the open in the closed stated state shown in FIGS. 1 to 7. Via the coupling and via the cog wheel segments 18, 20 the other holding element 12, 14 is correspondingly moved along. In the closed state, the two holding elements 12, 14 then surround the two sides of the head so that the head is surrounded at least three sides by the two holding elements 12, 14 together with the supporting element 33 and is thus fixed in a desired position.

The supporting element 33 has the effect that the head is spaced from the coupling position at which the two holding elements 12, 14 are coupled via the cog wheel segments 18, 20 and can thus not be clamped. Thus, on the one hand injuries are prevented and on the other hand it is ensured that the adjustment of the holding elements 12, 14 can reliably take place.

After the two holding elements 12, 14 have been rotated in the closed state, they can be fixed in this position in particular via two belts 40, 42. The belts 40, 42 are guided at the ends of the holding elements 12, 14 opposite to the cog wheel segments 18, 20 through corresponding slots 44, 46. Via velcro fasteners the belts 40, 42 can respectively be adapted in lengths to the corresponding dimensions of the received head. The first belt 40 is in particular guided via the forehead of the head received in the receiving area 32 and the second belt 42 is guided around the chin. Thus, a secure reliable and injury-free fixing of the head takes place.

At both belts 40, 42 respectively at least one padding 48, 50 can be provided in a preferred embodiment. Likewise, one or a plurality of paddings 52, 54 can be arranged at each of the sides of the holding elements 12, 14 facing the head.

The holding elements 12, 14 are in particular formed of a flexible material so that they are not rigid and thus injuries are prevented. Further, the holding elements 12, 14 can adapt to the contour of the head in a given range.

In FIGS. 8 to 10, respectively a highly simplified illustration of the head support 10 is illustrated, wherein in particular the belts 40, 42 and the paddings 48 to 54 are not illustrated.

FIG. 11 shows a schematic, perspective illustration of a head support 100 according to a second embodiment. Elements having the same structure and the same function are identified with the same reference signs.

Figure 15:
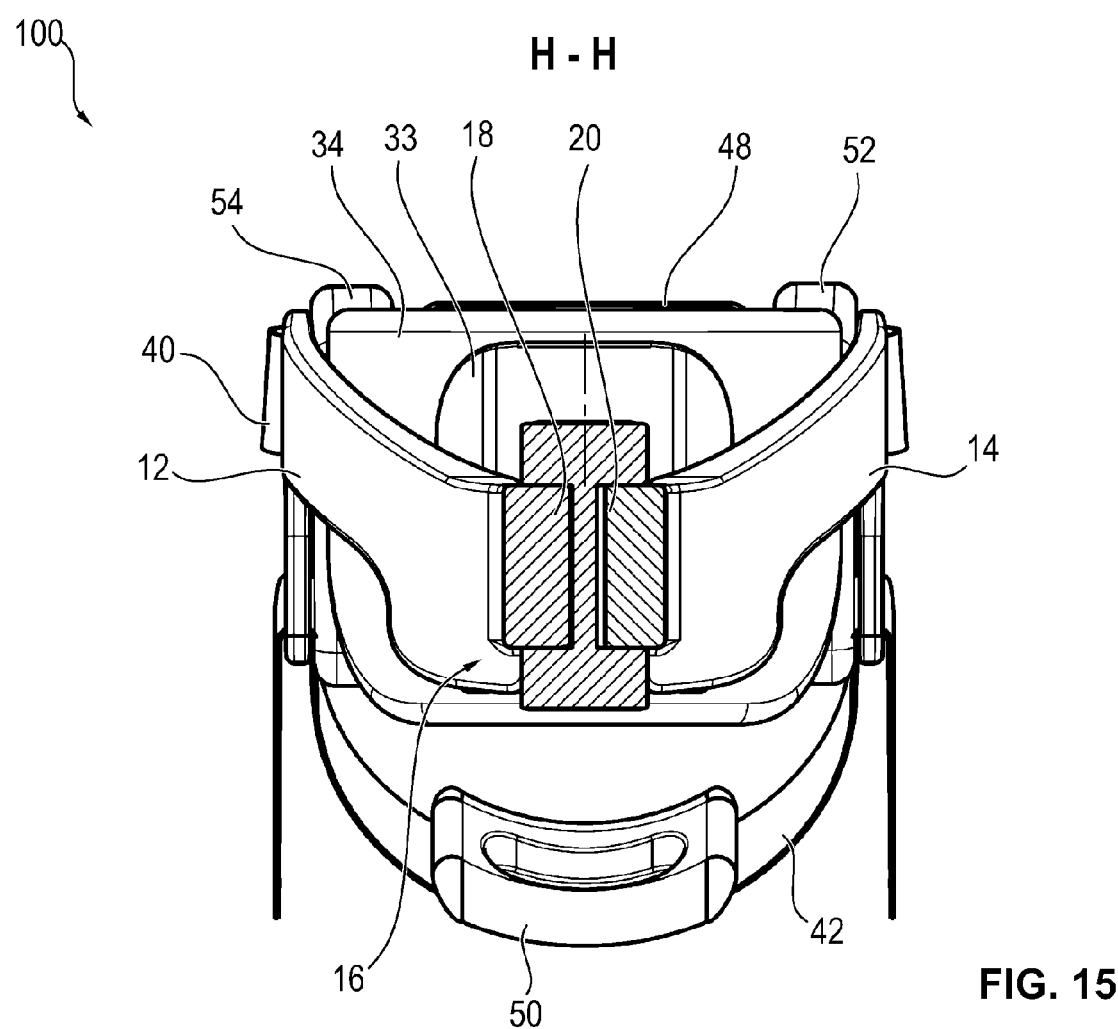
FIG. 15 a sectional rear view of the head support according to FIGS. 11 to 14 along the section H-H.

In FIG. 12, a front view of the head support 100 according to FIG. 11 is illustrated. FIGS. 13 to 15 respectively show a sectional illustration of the head support 100 according to FIGS. 11 and 12, wherein in FIG. 13 a front view, in FIG. 14 a side view and in FIG. 15 a back view is illustrated.

The second embodiment differs from the first embodiment only in that the second belt 42 is arranged in another angle due to a corresponding other arrangement of the slot 46.

In an alternative embodiment of the invention, also only one belt 40, 42 or no belt 40, 42 at all can be provided. Likewise, in an alternative embodiment, no padding 34 can be provided on the supporting element 33 and/or no paddings 48 to 54 can be provided at the holding elements 12, 14 and/or the belts 40, 42.

While the present invention has been illustrated and described with respect to a particular embodiment thereof, it should be appreciated by those of ordinary skill in the art that various modifications to this invention may be made without departing from the spirit and scope of the present.

What is claimed is:
1. A head support for operating tables, comprising:
  a first holding element rotatably mounted about a first axis of rotation for surrounding a first side of a patient's head receivable in a receiving area of the head support; and
  a second holding element rotatably mounted about a second axis of rotation for surrounding a second side of the patient's head;
  wherein the first holding element and the second holding element are coupled to each other in a coupling area by at least one coupling element such that when one of the holding elements is rotated, the coupling element also synchronously rotates the other holding element, the actuation of one of the holding elements causing a synchronous opening or closing of both the first and second holding elements;
  wherein a stationarily arranged supporting element for supporting the head receivable in the receiving area is provided between the coupling area and the receiving area; and
  wherein the synchronous opening or closing is caused by the first holding element meshing directly with the second holding element.

2. The head support according to claim 1, wherein the supporting element comprises an arcuate support surface for supporting the back of the head.

3. The head support according to claim 1, wherein the supporting element comprises a padding.

4. The head support according to claim 1, wherein the coupling element comprises at least one cog wheel segment.

5. The head support according to claim 1, wherein the coupling element comprises a first cog wheel segment firmly connected to the first holding element and a second cog wheel segment firmly connected to the second holding element, the first cog wheel segment and the second cog wheel segment being in engagement with each other.

6. The head support according to claim 5, wherein the first cog wheel segment and the first holding element, or the second cog wheel segment and the second holding element, are respectively formed integrally.

7. The head support according to claim 1, wherein said first holding element is formed mirror-symmetrically to the second holding element with respect to a middle plane of the head support.

8. The head support according to claim 1, wherein the head support comprises a fastening element for fastening on the operating table.

9. The head support according to claim 8, wherein the coupling element is arranged between the fastening element and the supporting element.

10. The head support according to claim 1, wherein a first belt for connecting the two holding elements is provided.

11. The head support according to claim 10, wherein a second belt for connecting the two holding elements is provided and the first belt surrounds the patient's forehead and the second belt surrounds the patient's chin.

12. The head support according to claim 11, wherein the first belt and the second belt are formed of an elastic material.

13. The head support according to claim 10, wherein:
the coupling element is arranged at a first end portion of the holding elements;
the first belt is arranged at a second end portion of the first holding element opposite to the first end portion of the first holding element; and
a second belt is arranged at a second end portion of the second holding element opposite to the first end portion of the second holding element.

14. The head support according to claim 1, wherein the holding elements surround the patient's head at at least three sides in a closed state, and the holding elements do not surround the head in an open state.

15. The head support according to claim 14, wherein the coupling element and the holding elements are designed such that the holding elements in the open state serve as supports for the arms of a person treating the patient.

16. A head support for operating tables, comprising:
a first support member rotatably mounted about a first axis of rotation for surrounding a first side of a patient's head receivable in a receiving area of the head support; and
a second support member rotatably mounted about a second axis of rotation for surrounding a second side of the patient's head;
wherein the first support member and the second support member are coupled to each other in a coupling area by at least one coupling member such that when one of the support members is rotated, the coupling member also rotates the other support member;
wherein the first support member and the second support member are flexible arms; and
wherein the coupling member includes at least one wheel.

17. The head support according to claim 16, wherein a stationarily arranged supporting element for supporting the head receivable in the receiving area is provided between the coupling area and the receiving area.

18. A head support for operating tables, comprising:
a first support member rotatably mounted about a first axis of rotation for surrounding a first side of a patient's head receivable in a receiving area of the head support; and
a second support member rotatably mounted about a second axis of rotation for surrounding a second side of the patient's head;
wherein the first support member and the second support member are coupled to each other in a coupling area by at least one coupling member such that when one of the support members is rotated, the coupling member also rotates the other support member, the actuation of only one of the support members causing a synchronous movement of both the first and second support members;
wherein a stationarily arranged supporting element for supporting the patient's head receivable in the receiving area covers the coupling area and is in a stationary position that blocks the patient's head from contacting the coupling area; and
wherein the synchronous movement is caused by a plurality of teeth of the first support member meshing with a plurality of teeth of the second support member.

19. The head support according to claim 18, wherein the head support encircles the patient's head in a closed state, and the head support does not encircle the head in an open state.

20. The head support according to claim 18, wherein a synchronous closing or opening of the two support members occurs when one of the support members is moved.

* * * * *